United States Patent [19]

Katz et al.

[11] Patent Number: 4,496,654
[45] Date of Patent: Jan. 29, 1985

[54] DETECTION OF HCG WITH SOLID PHASE SUPPORT HAVING AVIDIN COATING

[75] Inventors: David H. Katz, La Jolla; Steven W. Cooper; Theodore T. Lee, both of San Diego; Shung-Ho Chang, Encinitas, all of Calif.

[73] Assignee: Quidel, La Jolla, Calif.

[21] Appl. No.: 483,231

[22] Filed: Apr. 8, 1983

[51] Int. Cl.$^3$ ............................................. G01N 33/54
[52] U.S. Cl. ......................................... 435/7; 422/56; 435/805; 435/810; 436/530; 436/808; 436/810; 436/818
[58] Field of Search ................... 435/7, 805; 436/818; 422/56

[56] References Cited

U.S. PATENT DOCUMENTS 4,216,245  8/1980  Johnson ................................. 422/56
4,298,685 11/1981  Parikh ..................................... 435/7

Primary Examiner—Sidney Marantz
Attorney, Agent, or Firm—Hubbard & Stetina

[57] ABSTRACT

Human chorionic gonadotropin (HCG) is detected by enzyme immunoassay by bonding biotinylated antibody to an avidin coupled paper disc, reacting the antibody on the disc with the solution suspected of containing HCG, and determining the amount of HCG on the disc by enzymatic assay detection techniques.

16 Claims, 1 Drawing Figure

DETECTION OF HCG WITH SOLID PHASE SUPPORT HAVING AVIDIN COATING

FIELD OF THE INVENTION

This invention relates generally to enzyme immunoassay (EIA) techniques, and to the determination of human chorionic gonadotropin (HCG) in particular.

BACKGROUND

Enzyme immunoassay (EIA) methods have been described, Guesdon J., Ternynck, T., Avrameas, S., "The Use of Avidin-Biotin Interaction in Immunoenzymatic Techniques," *J. Histochem Cytochem* 27:1131–1139, 1979. Guesdon et al tested the effects of labeling antibodies, antigens and enzymes with biotin in EIA procedures. The biotin-avidin interaction is well-known and has been studied rather exhaustively, and has been used in purification of reagents by coupling avidin to a Sepharose chromatographic column, conjugating biotin to a protein to be purified, binding the biotinylated protein to the column, washing the column, and then eluting the purified protein-biotin conjugate protein from the column. Liu, F., Zinnecker, M. Hamaoka, T. and Katz, D. H., *J. Biochemistry* 18:690, 1979.

The measurement of HCG in serum or urine is of interest in the diagnosis of early pregnancy, detection of ectopic pregnancies, and in monitoring various tumors. Walsh, P. R., Wang M., Gittermann, M. L., CLINICAL IMMUNOCHEMISTRY, American Association for Clinical Chemistry, 1978, Natelson, S. et al, Eds., pp. 306–328.

The use of filter papers, usually in the form of small discs, in various assay procedures is well-known. However, efforts to develop an assay method for HCG using filter paper discs has not been successful. After considerable work, it was discovered that the methods based upon binding HCG antibody to a disc and reacting the disc with a solution suspected of containing HCG, e.g., urine, were of poor reliability and sensitivity. Moreover, discs and filter paper devices cannot be manufactured by known techniques in a satisfactory manner. The present invention overcomes these disadvantages and makes possible a rapid, reliable and simple enzyme immunoassay for HCG in urine, or other solution.

SUMMARY OF THE INVENTION

A method has been developed for determining chorionic gonadotropin (HCG) which is highly sensitive, extremely simple to carry out, and can be adopted to home use kits. The invention comprises the method and a kit or system for carrying out this detection. The concept of this invention has broader application to specific antigen determinations, and can also be adapted for determination of antibodies using the same concept by simply reversing the role of the antigen and antibody.

The method of this invention, exemplified by the determination of human chorionic gonadotropin (HCG) comprises, in its most preferred form: Coating all or part of a solid phase support with avidin, by chemical bonding, physical absorption or any other suitable technique, attaching biotinylated anti-HCG antibody to the support through the avidin-biotin coupling, exposing the support thus prepared to a sample, e.g., a solution, suspected of containing HCG and to labelled anti-HCG antibody. The result is a solid phase support having bound thereon HCG and a detectable label which is present in proportion to the amount of HCG substrate or developer for the label, or counted if the label is radioactive, as a measure of the concentration of HCG in the sample. Alternatively, the labeled species may be removed from the support and detected in any conventional manner. Enzyme labelling, e.g., with $\beta$-galactosidase, is a preferred approach, but other enzymes and radiolabels may be used.

The invention can also be utilized in the technique for determining the presence or absence, and measuring the quantity of antibodies. In this instance, an antigen to the specific antibody is biotinylated and bound through avidin to a support, a like antigen is labelled and the reaction is carried out in the same manner, except that the antibody is the species to be determined.

DESCRIPTION OF THE PREFERRED EMBODIMENT

Figure 1:
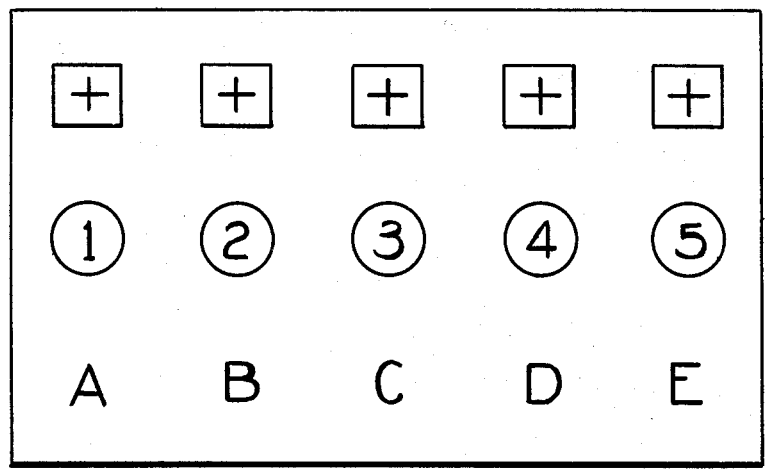
FIG. 1 depicts a solid phase support, which is coated in whole or in part with avidin, and upon which biotinylated antibody is coated in selected areas, depicting some exemplary patterns which may be formed by printing or otherwise applying the biotinylated antibody in predetermined areas.

The solid phase supports in the assay are, in this example, paper discs approximately 0.7 cm in diameter, Whatman (Trademark) grade 541. The paper discs are first activated with CNBr according to the procedure described by R. Axen et al. (*Nature*, 214:1302, 1967). The activated discs were allowed to react with avidin at 4° C. overnight. After reaction, the solution was removed and the discs were blocked with 50 mM ethanolamine, pH=8.0, at room temperature for 2 hours. The discs were then washed extensively with 0.1M NaOAC, 0.5M NaCl buffer, pH=4.0, and 0.1M NaHCO$_3$, 0.5M NaCl buffer, pH=8.3, alternately, 3 times.

Biotinylation of affinity purified rabbit anti-HCG antibody was accomplished by incubation of the antibody with N-hydroxysuccinimidyl-biotin in borate buffered saline (BBS) at pH=8.3 at room temperature for 2 hours. Excess N-hydroxysuccinimidyl-biotin was then removed by dialysis or gel filtration.

$\beta$-Galactosidase-linked antibody was prepared by reacting affinity purified mouse anti-HCG monoclonal antibody with $\beta$-galactosidase through a cross-linking reagent M-Maleimidobenzol-N-Hydroxysuccinimide (MBS) according to procedure published by F. T. Liu et al., *J. Biochemistry* 18:690 (1979).

The immunoassay is accomplished by the interactions of the assay components as described below:

In a typical Disc-Avidin Biotin-Ab-HCG-Ab-$\beta$-Galactosidase (HCG EIA) example, the disc resides in a chamber with a lyophilized pellet of Anti-HGC-$\beta$-Galactosidase, 250 $\mu$l of urine sample is used to dissolve the pellet and rehydrate the disc. The disc-avidin-biotin-Anti HCG (BAD), the anti-HCG-$\beta$-Galactosidase, and the urine sample incubate simultaneously at room temperature for 10 minutes. The disc is then removed and washed extensively with a buffer solution or under a stream of tepid water. The disc is finally incubated with O-nitrophenyl-galactopyranoside (ONPG), a synthetic substrate for $\beta$-Galactosidase. The enzyme activity is related to the amount of HCG present in the urine sample.

A dose-response curve has been demonstrated using the above protocol. For qualitative assays, urine sample with 400 mIU/ml HCG can be easily detected with the naked eye. This HCG level corresponds to approximately 3 days after missed period.

One feature of the invention is the application of the method and protocol to a kit which can be used by an untrained individual in the privacy of her own home to detect the presence or absence of HCG as an indicator of possible pregnancy. As the above protocol indicates, this detection can be made as early as three days after a menstrual period has been missed. A missed period may indicate pregnancy, and it may also indicate a possible complication, in some individuals an early indication of pregnancy is important. There has been a long standing need for a kit which can be used without need for a laboratory or skilled technicians. Kits may also be used in or out of the clinic or laboratory to monitor various tumors.

Kits include all reagents necessary to complete a qualitative or semi-guantitative determination of HCG in urine. The basic constituents of a kit are: (1) Solid phase support, typically filter paper discs, treated with avidin, the avidin being bound to the paper to provide sites which are reactor with biotinylated anti-HCG antibody; (2) Labeled anti-HCG antibody; (3) Wash reagents; and (4) Developing reagent. In the case given as a preferred embodiment, which is exemplary and non-limiting, the developing reagent is O-nitrophenyl-galactopyranoside (ONPG). Development of a $\beta$-galactoside labeled HCG-antibody species provide a color change which is visible to the naked eye. Other color, or visible effect producing label and developer combinations may be applied; however, the system described is presently preferred. Buffers, saline reagents, etc. may also be included but it is preferable to incorporate these into the various reagents described above. Kits, according to this invention, would typically include a vessel having a predetermined volume indication, instructions for use, and such accessories as may be convenient for the user.

FIG. 1 depicts an example of an article of manufacture, such as component of a kit, which embodies a principle of this invention. The device depicted in FIG. 1 comprises the solid phase support, a layer of avidin, and a layer of biotinylated antibody (or antigen if an antibody is to be detected). Of course, these many layers need not be perfectly congruent with one on the other and, if the substrate were porous, would not be physically discrete layers but in effect would have the described structure. The substrate may be porous or non-porous. For example, filter paper and polystyrene may both serve very well.

Any solid phase material which is inert in the reactions, and to which avidin can be bound, either by chemical reaction or physical attachment, may be used. Filter paper discs or sheets are a common solid phase support material as are discs or plates of polystyrene.

The next component is biotinylated antibody (or antigen) which is not coated over the entire surface, as was the case in the earlier described examples. Rather the biotinylated antibody (or antigen) is "printed" on only selected areas of the avidin coated surface in any desired pattern. The term "printed" is used to describe the best known technique for manufacturing the multiple indicator substrate of this invention, and the ability to "print" the antibody on selected areas is a very important feature of this invention. It has been extremely difficult to provide any reliable pattern on filter papers or other substrates because the reagent migrates through or across the substrate. The present invention obviates this entire problem. The biotinylated antibody couples immediately with the avidin, thereby fixing the area on the avidin coated support where a particular antibody will be found. This coupling prevents migration during or after printing, and during reaction, of the antibody (or antigen). Thus, upon development of the multiple indicator substrate, the antibody, and any antigen to which it is bound, will be found exactly where it was printed. Printing may be acccomplished in the same manner that ink is printed on paper, i.e., by application on type or other patterned means coated with the biotinylated antibody to the avidin coated support. This permits very efficient, high volume production of multiple indicator support, which may have several different antibodies found thereon. The substrate may include indicia formed of ink or other material as well as the indicia formed of antibody (or antigen). In FIG. 1, for example, the top and center rows indicate, respectively, square or round areas having some other indicia therein upon which the biotinylated antibody is printed, while the lower row indicates biotinylated antibody printed in the form of letters. Obviously, any symbol, shape or alphanumeric indicia may be used.

These multiple indicator substrates may be used in the clinical or research laboratory, or may be included in a kit for consumer use. Several different antibodies (or antigens), and antibodies of different activity may be printed on the substrate, thus permitting, with one such multiple indicator substrate, several diagnostic tests to be performed at one time, or give semi-quantitative results respecting a particular antigen or antibody.

DISCUSSION

Efforts to provide a procedure and a kit in which the HCG was bound to a solid, fibrous substrate, such as filter paper (which is available in high purity and convenient sizes) were not successful. Two problems plagued the method to the point that the approach was being considered unfeasible. First, low sensitivity was a serious concern. Secondly, and even more serious, was the poor reproducibility. After considerable effort, and consideration of the problem, the inventors determined that the problems were somehow involved in the binding of the reagents to the filter paper. It is not known for certain what the problem is, fundamentally, and no problem was considered likely since it is relatively easy to bind antigen to filter paper, or equivalent porous members. It is postulated, only as a possible explanation, which has not been proven by firm data, that some type of steric hindrance occurs when antibody is bound to the paper which prevents complete, quantitative and reproducible reaction of the treated filter paper by the antibody. In any event, regardless of the actual molecular phenomenon which occurred, poor sensitivity, and a narrow assay range was the result. This immunoassay range did not seem profitable to pursue. In addition, the requirements for individual coupling, handling and storage of solid phase antibodies for different immunoassays was considered prohibitively time consuming and costly.

After consideration of the problem, and various evaluations of alternative approaches, and upon experimentation, the technique set forth above was developed by the inventors, and was proved out as a viable, simple, reliable and reproducible method of high sensitivity which finds direct application to the determination of HCG in urine, and has greater applicability for other antibody-antigen type reactions. As pointed out above, the same procedure, reversed to bind the antigen to the paper through biotin-avidin coupling, rather than the antibody binding described above, may be used to detect the presence of an antibody. Thus, the terms antigen and antibody may be substantially reversed in the specification and claims to give the fully equivalent, converse of the specific terms used above and hereinafter.

The general applicability of the present invention has been established. For example, an avidin coated substrate was coated with biotinylated-AntiDNP-IgG. This avidin-biotinylated-AntiDNP-IgG coated substrate was then reacted with $DNP_{49}$-BSA and finally with Anti-DNP-$\beta$-galactosidase. The presence of $DNP_{49}$-BSA was determined in the final reaction by production of color on the coated area of the substrate. The results can be quantitatively determined by reading the absorbance of the color at 420 nm in the conventional manner.

In another example, the avidin coated portion of a substrate was coated with biotinylated ragweed allergen, then incubated simultaneously with human serum containing Anti-Ragweed allergen-IgE and with goat-Anti-Human IgE-$\beta$-galactosidase. The presence of Anti-Ragweed IgE is determined by the color produced in the area coated as described, and can be measured photometrically as described above.

It will be understood that in giving the preferred embodiment and application of the invention the concept and scope of the invention is exemplified thereby without being limited to the specific reagents, labels, developers, or applications.

What is claimed is:

1. In the method for determining human chorionic gonadotropin (HCG) which comprises reacting a solution suspected of containing HCG with labeled anti-HCG antibody and determining the presence of HCG bound antibody, the improvement comprising:
   (a) coating a solid phase support with avidin to provide on the surface thereof binding sites for biotin;
   (b) biotinylating anti-HCG antibody;
   (c) reacting the biotinylated anti-HCG antibody with the avidin coated support;
   (d) labeling anti-HCG antibody with indicator moiety which can be detected;
   (e) reacting the biotinylated antibody of step (c) and the labeled antibody of step (d) with a test solution suspected of containing HCG; and
   (f) measuring the labeled antibody bound through HCG to the support to show the presence or absence of human chorianic gonadotropin in the test solution.

2. A method of determining HCG, human chorionic gonadotropin, comprising treating a solid phase support with avidin to provide on said solid phase support with avidin bound sites capable of binding biotin to said solid phase support, biotinylating anti-HCG antibody; reacting a solution suspected of containing HCG with an indicator reagent which will bind to HCG and with said biotinylated anti-HCG antibody with said support to bind HCG to the solid phase support through the avidin-biotin couple, and measuring by means of the indicator moiety of the indicator reagent the presence or absence of HCG on said solid phase support.

3. A method for detecting the presence or absence of a specific antigen in a test solution suspected of containing such specific antigen, comprising the steps of:
   (a) reacting a solid phase support with avidin to bind the avidin to the support to provide sites on said solid phase support capable of coupling with biotin for binding biotinylated molecules to said filter member;
   (b) biotinylating antibody to the specific antigen to provide a molecule capable of binding to avidin sites on the solid phase support;
   (c) reacting the species of step (b) with the avidin treated solid phase support of step (a) to thereby bind said species to said solid phase support;
   (d) labeling antibody to the specific antigen with a moiety capable of being detected;
   (e) reacting the test solution suspected of containing the specific antigen with the treated solid phase support resulting from step (c) and the reagent from step (d) to form a species which includes specific antigen, the biotinylated antibody on the support, and the labeled antibody; and
   (f) detecting the labeled moiety of the antibody to thereby determine the presence or absence of the specific antigen in the test solution.

4. The method of claim 3 wherein the specific antigen to be determined is human chorionic gonadotropin.

5. The method of claim 3 wherein the moiety capable of being detected is $\beta$-galactosidase.

6. A kit for use in determining the presence or absence of HCG, human chorionic gonadotropin, in urine, comprising:
   (a) biotinylated anti-HCG antibody bound to an avidin treated support;
   (b) labeled anti-HCG antibody; and
   (c) developing reagent capable of reacting with the labeled anti-HCG antibody to give a visual indication of the presence or absence of HCG.

7. The kit of claim 6 wherein the anti-HCG antibody is labeled with $\beta$-galactosidase as a detectable label.

8. The method of manufacturing a multiple indicator support comprising the steps of:
   (a) coating at least a portion of a solid phase support with avidin; and
   (b) coating only predetermined portions of the avidin coated support of step (a) with biotinylated antibody or biotinylated antigen, thereby leaving portions of the support uncoated thereby forming a predetermined pattern of areas of biotinylated antibody or antigen coated support.

9. The method of claim 8 wherein:
   step (a) comprises coating substantially one surface of a generally planar support with avidin, and
   step (b) comprises printing a predetermined pattern of biotinylated antibody or biotinylated antigen on said one surface.

10. The method of claim 9 wherein:
   step (a) comprises coating a filter paper with avidin.

11. As an article of manufacture, a solid phase support having a surface, an avidin coating on at least substantial portions of said surface, and biotinylated antibody or biotinylated antigen printed in a predetermined pattern on the avidin coated surface.

12. The article of manufacture of claim 11 wherein the support surface is substantially totally coated with avidin, and wherein the biotinylated antibody or biotinylated antigen pattern occupies substantially less than all of said surface.

13. The article of manufacture of claim 11 or claim 12 wherein the biotinylated antibody or biotinylated antigen pattern is in the form of readable symbols, numerals, or letters, or a combination thereof.

14. In the determination of immunologically active species, the steps of:
(a) coating a surface of a solid phase support with avidin,
(b) printing a biotinylated antibody or biotinylated antigen on said avidin support in a predetermined pattern,
(c) reacting the biotinylated antibody or biotinylated antigen coated surface with a solution suspected of containing the immunologically active species and with a labeling moiety, and
(d) reacting the labeling moiety with a developer reagent.

15. A kit for use in detecting antigen, comprising:
(a) a solid phase support having coated thereon a layer of avidin and reacted upon said layer of avidin biotinylated antibody to the antigen to be detected; and
(b) antibody to the antigen to be detected labeled with a moiety capable of being detected.

16. The kit of claim 15 wherein the labeled antibody includes an enzyme moiety and wherein the kit further includes:
(a) a developing substrate which develops a color when reacted with the labeling enzyme.

* * * * *